United States Patent [19]
Abraham

[11] Patent Number: 5,849,560
[45] Date of Patent: Dec. 15, 1998

[54] PROTEASES CAUSING DEGRADATION OF AMYLOID β-PROTEIN PRECURSOR

[75] Inventor: Carmela R. Abraham, Lexington, Mass.

[73] Assignee: Trustees of Boston University, Boston, Mass.

[21] Appl. No.: 25,321

[22] Filed: Feb. 26, 1993

Related U.S. Application Data

[63] Continuation-in-part of Ser. No. 681,093, Apr. 5, 1991, Pat. No. 5,200,339, which is a continuation-in-part of Ser. No. 568,806, Aug. 17, 1990, abandoned.

[51] Int. Cl.$^6$ .............................. C12N 9/50; C12N 9/48
[52] U.S. Cl. ........................................... 435/219; 435/212
[58] Field of Search ...................................... 435/212, 219

[56] References Cited

U.S. PATENT DOCUMENTS 5,252,463  10/1993  Nelson et al. ............................ 435/23
5,292,652   3/1994  Dovey et al. ........................... 435/226

FOREIGN PATENT DOCUMENTS 9207068  4/1992  WIPO .

OTHER PUBLICATIONS

Pierotti et al. (1990) *Biochemistry*, 29(45), 10323–10329.
Barrett et al. (1990) *Biochem. J.* 271, 701–706.
Orlowski et al. (1989) *Biochem. J.* 261, 951–958.
Backstrom et al. (1992) *J. Neurochem.* 58(3), 983–992.
McDermott et al. (1991) *Biochem. Biophys. Res Comm*, 179(3) 1148–1154.
Nelson et al. (1989) *J. Neurochem.*, 53(2), 641–647.
Beinfeld et al. (1989) *Biochem. Biophys. Res. Comm.*, 160(2), 968–976.
Seubert et al. (1992) *Neurobiol. Aging, 3rd Int'l Conf.*, 13(Suppl), 580, Abst. 317.

*Primary Examiner*—John W. Rollins
*Assistant Examiner*—Jon P. Weber
*Attorney, Agent, or Firm*—Choate, Hall & Stewart

[57] ABSTRACT

A proteolytic factor has been isolated from the brains of humans with Alzheimer's disease which specifically cleaves the peptide having the sequence His-Ser-Glu-Val-Lys-Met-Asp-Ala-Glu-Phe (SEQ ID NO: 1) between Met and Asp. This peptide is in the cleavage site of the N-terminal domain of the amyloid β-protein precursor.

3 Claims, 9 Drawing Sheets

Cathepsin G    H  S  E  V  K  M  D  A  E  F
                     ▲     ▲  ▲  ▲
                     3    100 46  7
CASP           H  S  E  V  K  M  D  A  E  F
                  ▲        ▲  ▲  ▲
                  9       21 18 34
FIG. 4
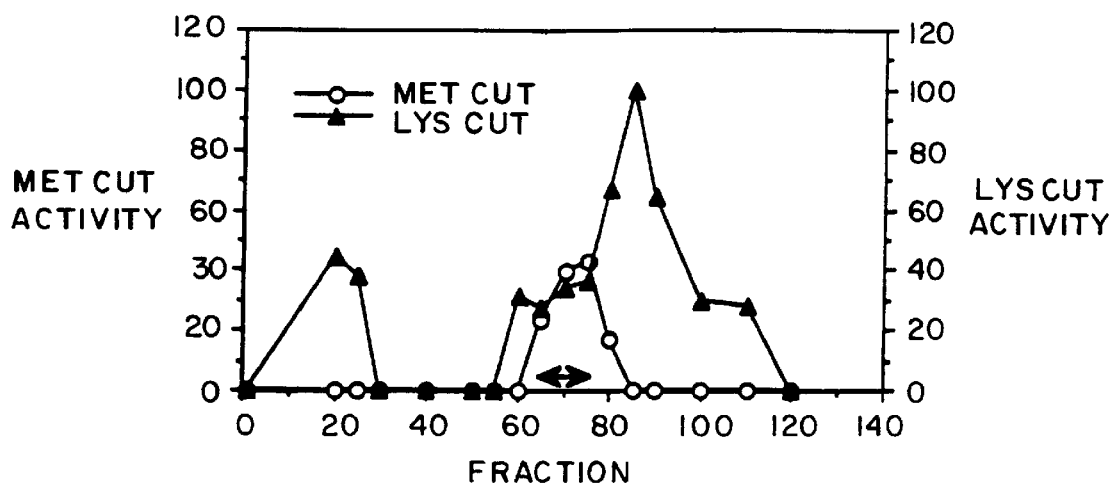
FIG. 8
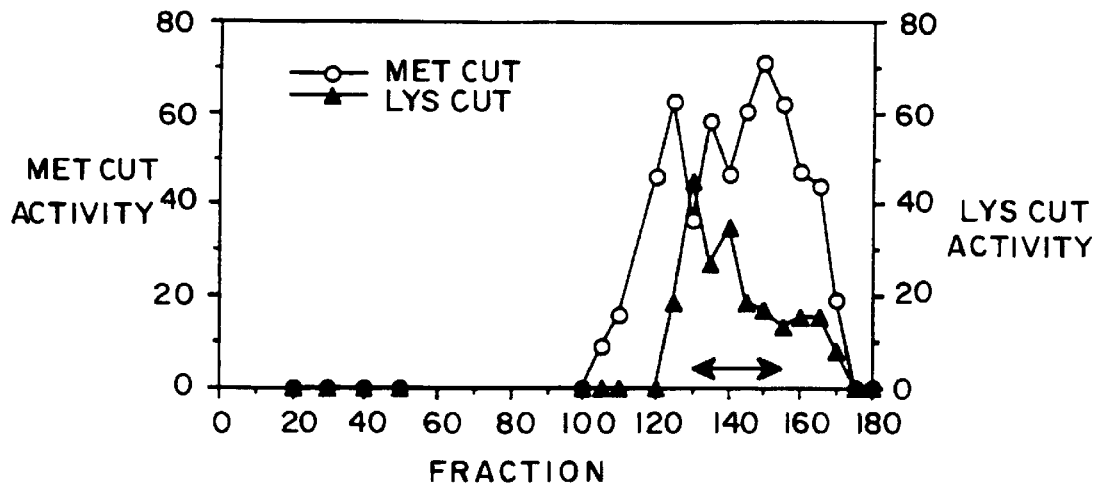
FIG. 9

PROTEASES CAUSING DEGRADATION OF AMYLOID β-PROTEIN PRECURSOR

This application is a continuation-in-part of my application U.S. Ser. No. 681,093, filed Apr. 5, 1991, now issued as U.S. Pat. No. 5,200,339, which is a continuation-in-part of U.S. Ser. No. 568,806, filed Aug. 17, 1990, now abandoned.

BACKGROUND OF THE INVENTION

This invention was made during the course of work supported in part by the U.S. Government, and the Government has certain rights in the invention.

This invention relates to treatment of Alzheimer's disease.

The brains of persons having Alzheimer's disease and Down's syndrome and, to a far lesser extent, the brains of normal aged persons exhibit abnormal extracellular proteinaceous deposits, termed amyloid. Amyloid deposits are thought to be trophic or toxic to their surroundings.

Amyloid deposits are found in the center of senile plaques and in the blood vessels in the brains of Alzheimer's disease ("AD") patients. The major component of brain amyloid is the β-protein, a 4 kDa (39–42 amino acids) fragment (see, e.g., Glenner et al. (1984), *Biochem. Biophys. Res. Comm.*, Vol. 12, pp. 1131–35; Masters et al. (1985), *Pro. Natl. Acad. Sci. USA*, Vol. 82, pp. 4245–49; Selkoe et al. (1986), *Jour. Neurochem.*, Vol. 46, pp. 1820–34; Roher et al. (1986), *Proc. Natl. Acad. Sci. USA*, Vol. 83, pp. 2662–66, all hereby incorporated herein by reference), derived from a larger, 110–135 kDa β-protein precursor ("β-PP") (see, e.g., Goldgaber et al. (1987), *Science*, Vol. 235, pp. 877–80; Kang et al. (1987), *Nature*, Vol. 325, pp. 733–36; Robakis et al. (1987), *Pro. Natl. Acad. Sci. USA*, Vol. 84, pp. 4190–94; Tanzi et al. (1987), *Science*, Vol. 235, pp. 880–83, all hereby incorporated herein by reference). In addition to and tightly associated with the β-protein, brain amyloid also contains a serine protease inhibitor, α1-antichymotrypsin ("ACT").

Certain β-PP transcripts include a domain homologous to the Kunitz-type protease inhibitors (described, for example, in Kitaguchi et al. (1988), *Nature*, Vol. 331, pp. 530–32; Ponte et al. (1988), *Nature*, Vol. 311, pp. 525–27; Tanzi et al. (1988), *Nature*, Vol. 331, pp. 528–30). The normal physiologic C-terminal cleavage that releases the secreted form of β-PP (PN2) occurs within the β-protein domain, and outside the putative membrane domain.

M. Tsudo et al. (1987), *Pro. Natl. Acad. Sci. USA*, Vol. 84, pp. 4215–18) describe crosslinking a ligand and a receptor site for the ligand by treatment with disuccinimidyl suberate ("DSS").

SUMMARY OF THE INVENTION

We have discovered proteolytic factors from the brain of AD patients, here termed "AD proteolytic factors". According to the invention accumulation of the β-protein is a consequence of an alternative degradation pathway that results in accelerated β-PP processing, and one or more of the AD proteolytic factors participates in this pathway.

In general, in one aspect, the invention features an AD proteolytic factor capable of cleaving β-protein precursor at a site near the β-protein N-terminus. In preferred embodiments the AD proteolytic factor is capable of cleaving β-PP at a site outside the β-protein domain and near the β-protein N-terminus, more preferably at a site following lysine or at a site following methionine; a first AD proteolytic factor includes a calcium-activated protease, preferably a serine protease; activity of the serine AD proteolytic factor is inhibited by PN2 and by ACT; a second AD proteolytic factor includes a metalloprotease; the metalloprotease is $Zn^{2+}$ dependent and $Mg^{2+}$ stimulated, requires having one or more cysteine residues in the reduced state for activity, and has a molecular weight of about 85 kDa.

In another general aspect, the invention features a method for treating Alzheimer's disease in a patient, by reducing β-protein precursor proteolysis at a site near the β-protein N-terminus. In preferred embodiments, the method includes administering to the patient an inhibitor that inhibits proteolysis at a site outside the β-protein domain of β-PP and at or near the β-protein N-terminus ("near" is within five amino acids of the β-protein N-terminus), and preferably inhibits proteolysis in the vicinity of the β-protein N-terminus, preferably by inhibiting the proteolytic activity of a proteolytic factor that acts at such a site; the inhibitor is capable of passing the blood-brain barrier, and the inhibitor can be administered, for example, parenterally (intravascularly or intramuscularly) or orally.

In another general aspect, the invention features a method for diagnosis in a subject of a disease characterized by accumulation of amyloid, and particularlyof Alzheimer's Disease, by determining the level, in a sample from the subject, such as a tissue or fluid sample, of an AD proteolytic factor.

In another general aspect, the invention features a method for screening for an agent useful in treatment of a disease characterized by accumulation of amyloid, by incubating an AD protease with a peptide having an amino acid sequence corresponding to the sequence spanning the β-protein N-terminus in the presence of the candidate agent, and determining degradation of the peptide. A candidate agent may be useful in treating such a disease where peptide degradation by the AD protease is less in the presence of the candidate agent than would have been expected under the same or similar reaction conditions in the absence of the candidate agent.

In preferred embodiments the peptide has an amino acid sequence that includes a 10-amino acid sequence spanning the β-protein N-terminus, and more preferably beginning five or six amino acids upstream from the N-terminus.

In another general aspect, the invention features a method for purifying an enzyme from a sample, and particularly a proteolytic enzyme, by incubating the sample with a substrate of the enzyme or with a fragment of the substrate to which the enzyme binds, treating the sample with DSS to crosslink any enzyme-substrate complexes in the sample, and recovering the complexes. In preferred embodiments the substrate or substrate fragment is labelled (more preferably radiolabelled).

DESCRIPTION OF PREFERRED EMBODIMENTS

Drawings

FIG. 1 is a series of prints showing serine protease activity in fractions initially purified from brain homogenates from Alzheimer's disease ("AD") patients. Panel A is a photograph of a coomassie blue stained SDS-PAGE gel showing brain homogenates fractions following reaction with the iodinated peptide $^{125}$I-His-Ser-Glu-Val-Lys-Met-Asp-Ala-Glu-Phe (peptide "P1") (SEQ. ID. NO: 1) and cross-linking with disuccinimidyl suberate ("DSS"). Panel B is an X-radiograph of the gel prepared in Panel A. Panel C is an autoradiograph of a cellulose microcrystalline thin layer chromatography ("TLC") plate showing cleavage products of $^{125}$I-P1 following reaction with brain homogenate fractions.

FIG. 4 is a sequence map showing cleavage of P1 by cathepsin G (upper) and by $Ca^{2+}$ activated specific serine protease ("CASP") according to the invention (lower). Abbreviations: H, histidine; S, serine; E, glutamic acid; V, valine; K, lysine; M, methionine; D, aspartic acid; A, alanine; F, phenylalanine. Numerals show percentage cleavage of the peptide bond at each point indicated by an arrow.

Figure 5:
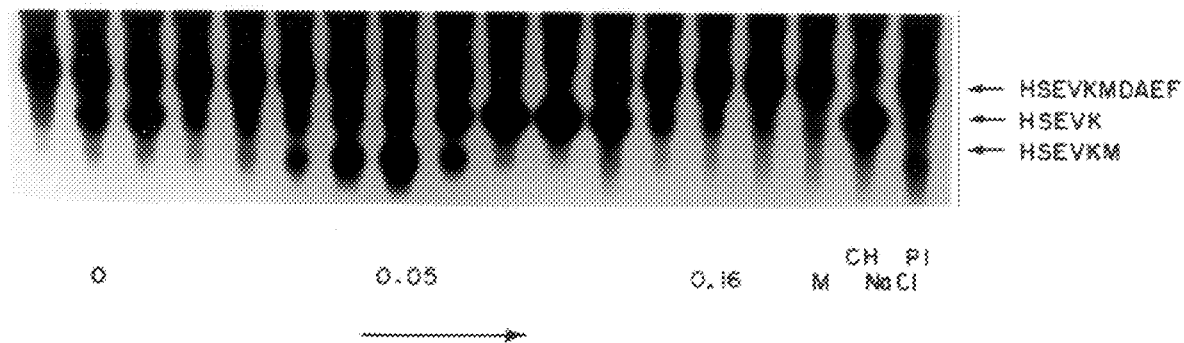

FIG. 5 is a print of a radiograph of a TLC plate showing metalloprotease activity in fractions purified using DEAE-Trisacryr® M (a 40–80 μm ion exchange resin produced by co-polymerization of N-acryloyl-2-amino-2-hydroxymethyl-1, 3-propanediol with an acrylic or anionic derivative, available from BioSepra, Marlborough , Mass.) ion exchange chromatography from brain homogenates from AD patients. Fractions eluted with a linear NaCl gradient, indicated by the arrow at the lower margin of the Fig., were incubated with radioiodinated P1 and separated on TLC. The sequences of uncleaved P1 and of the cleaved products are shown to the right.

Figure 6:
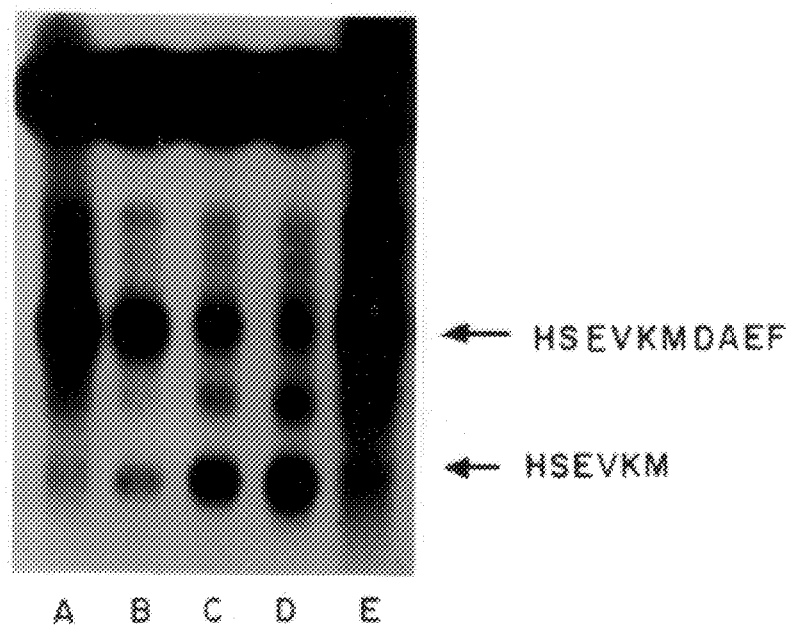

FIG. 6 is a print showing the influence of dithiothreitol ("DTT") on AD metalloprotease activity.

Figure 7:
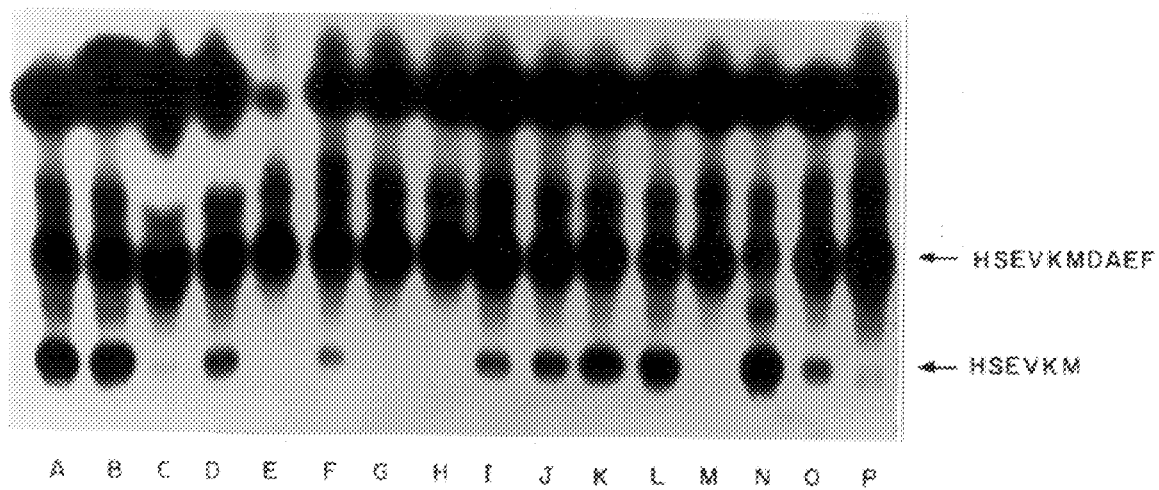

FIG. 7 is a print showing inhibition by various agents on metalloprotease activity in fractions from brain homogenates from AD patients.

FIG. 8 shows the activity profiles of DEAE-trisacryl M ion exchange chromatography of a 40 to 80% ammonium sulfate fraction of AD brain homogenate. The fractions containing metalloprotease activity ("Met cut") were pooled as indicated by the arrow.

FIG. 9 shows the activity profile of the phenyl Sepharose CL-4B (a cross-linked derivative of a 45–165 μm, 4% agarose gel filtration medium available from Pharmacia Biotech, Uppsala, Sweden)-column. The column was eluted with a linear gradient of 0.5 to 0M $(NH_4)_2SO_4$, and the active fractions were pooled as shown by the arrow.

Figure 10:
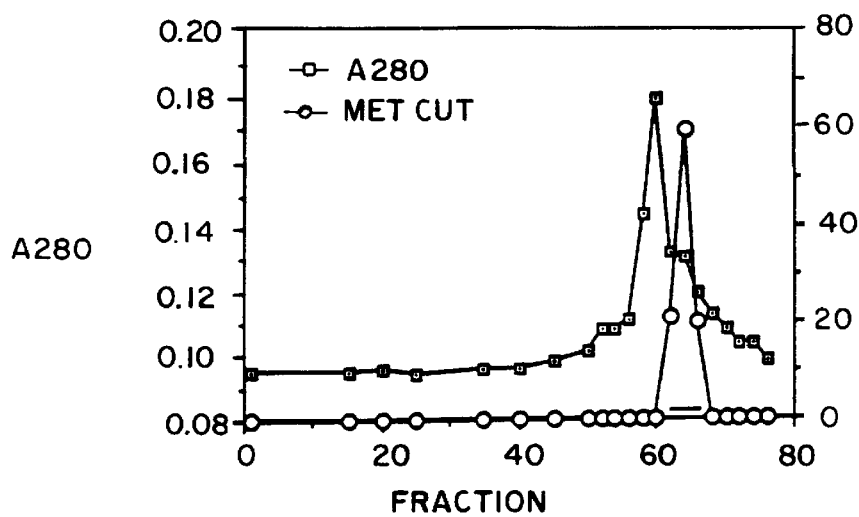

FIG. 10 shows the activity profile of the Sephacryl S-200 (a 47 μm gel filtration medium available from Pharnacia Biotech, Uppsala, Sweden) column fractions. Metalloprotease activity ("Met cut") fractions were pooled as indicated by the bar.

Figure 11:
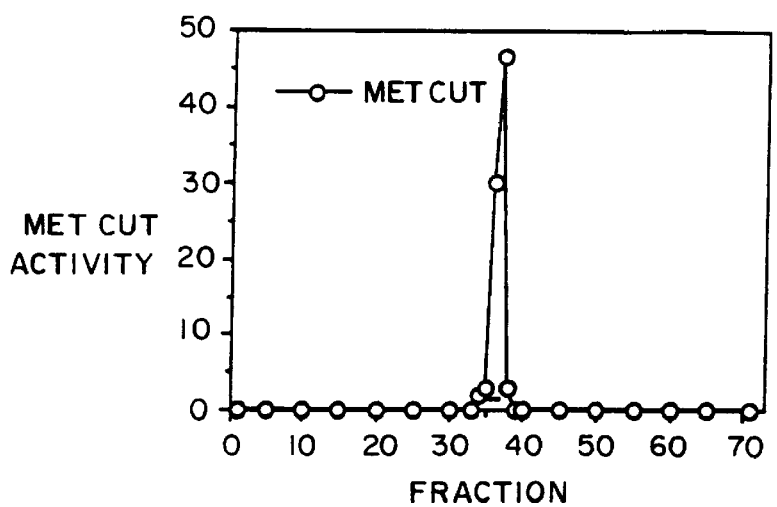

FIG. 11 shows the activity profile of the HA-Ultrogel (40% by weight microcrystalline hydroxyapatite in cross-linked 4% beaded agarose suspension in 1M NaCl containing 20% ethanol, available from Sigma Chemical Co., St. Louis, Mo.) hydroxyapatite column fractions. The metalloprotease activity ("Met cut") activity containing fractions were pooled. The active fractions of this column represent the final protease preparation.

Figure 12:
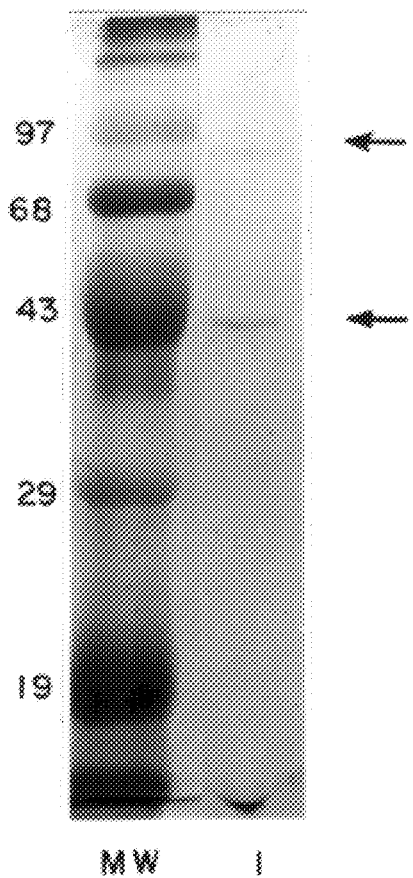

FIG. 12 is a photograph of a silver stained SDS-polyacrylamide gel of the purified protease preparation. The position of two protein species is indicated by arrows. MW, molecular weight standards; lane 1, purified protease sample.

Figure 13:
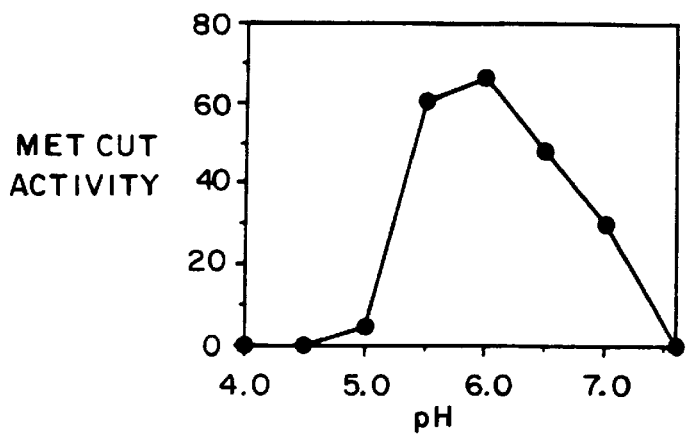

FIG. 13 shows the pH dependence of the purified "Met cut" metalloprotease. Protease activity was examined at different pH's with citrate/phosphate buffers, and the reactions were analyzed by TLC followed by autoradiography. Laser densitometry was used to quantitate the reactions, and the densitometric readings are represented graphically as "Met cut"activity.

Figure 14:
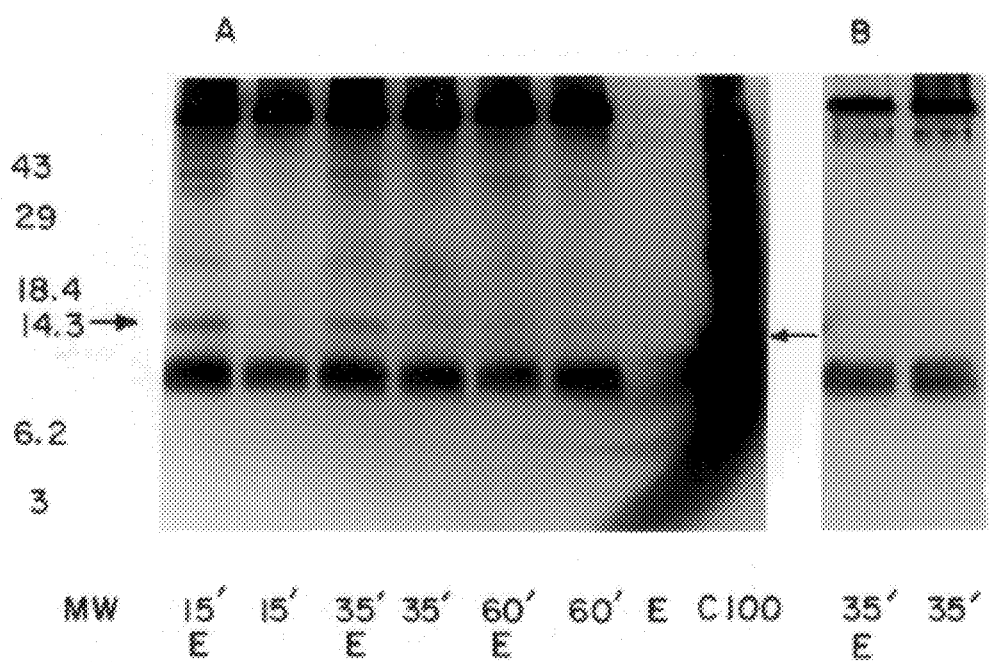

FIG. 14 shows the degradation of human recombinant β-PP by the "Met cut" metalloprotease. β-PP (1.6 μg) was incubated with the purified "Met cut" metalloprotease at physiological pH. Incubations were carried out at 37° C. for 15, 35 and 60 min. The reactions were separated on SDS-Tricine-PAGE and transferred to PVDF membranes. The blot was immunostained with rabbit antibodies targeting the last 30 amino acids of β-PP. Lane MW, molecular weight markers. Panel A: β-PP plus "Met cut" metalloprotease (E), or β-PP alone. The position of the 15 kDa proteolytic fragment is indicated by arrow. Lane C-100, recombinant polypeptide corresponding to the β-PP 596–695 amino acids (arrow). Panel B: β-PP plus "Met cut" metalloprotease (E) or β-PP alone were incubated for 35 min, transferred and stained with the same antibody after absorption with its antigen.

TABLES

Table I summarizes the purification of the "Met cut" metalloprotease when purified according to the second protocol.

Table II tabulates the activity of the "Met cut" metalloprotease when incubated with various divalent cations and protease inhibitors.

Table III is a comparison of the amino acid sequence of the peptides derived from proteolytic cleavage of the 85 kDa protein, with the homologous sequence from rat SEQ. ID Nos. 3 and 5. Human sequence peptide 85-1 is SEQ. ID No. 4 and human sequence peptide 85-2 is SEQ. ID No. 6.

Table IV is a comparison of the amino acid sequence of the peptides derived from proteolytic cleavage of the 43 kDa protein, with the homologous sequence from rat SEQ. ID Nos. 7 and 9. Human sequence peptide 43-1 is SEQ. ID No. 8 and human sequence peptide 43-2 is SEQ. ID No. 10.

Isolation and Purification of AD Metallo-proteolytic Factor

An AD proteolytic factor according to the invention can be identified in and isolated from a tissue homogenate using, for example, conventional liquid chromatography.

The following is a detailed description, presented by way of example, of two similar protocols for identifying and isolating an AD proteolytic factor from brain homogenate. It will be appreciated that protocols varying in detail from the protocols described here may be used to isolate and purify AD proteolytic factors that are within the scope of the invention.

Generally, the protocol in one embodiment includes steps of homogenizing the tissue; fractionating the homogenate with ammonium sulfate; making a crude separation using affinity liquid chromatography; further separating using a first DEAE-ion exchange column, followed by a gel filtration column, followed by a second DEAE-ion exchange column; and dialyzing and finally purifying using affinity liquid chromatography. The protocol in another embodiment includes steps of homogenizing the tissue; fractionating the homogenate with ammonium sulfate; separating using a DEAE-Trisacryl M ion exchange column; further separating using a phenyl sepharose CL-4B column; followed by a gel filtration column; and finally separating using a HA-ultrogel column.

The description also includes protocols for characterizing the purified AD proteolytic factor (molecular weight; substrate specificity; pH optimum) and for screening for useful inhibitors of the activity.

The protocols described in detail below have been used successfully to isolate and purify an AD metalloprotease from AD brain homogenate, the activity of which is dependent upon one or more cysteine residues being in the reduced state. This AD metalloprotease cleaves the P1 peptide after Met. It has a molecular weight about 85 kDa, and is a metalloprotein, being $Zn^{2+}$-dependent, and stimulated by $Mg^{2+}$ in vitro. Apparently, most cysteine protease inhibitors and some metalloprotease inhibitors effectively inhibit the AD metalloprotease purified from AD brain homogenates according to the following protocol.

Brain Homogenates

Brain tissue from AD patients is homogenized in ice-cold 5×(volume/weight) Tris-Cl or Tris-acetate buffer containing 1% Triton X-100 and 1 mM dithiothreitol ("DTT") in a Waring blender. After homogenization, the solution is stirred for 30 minutes on ice, and then centrifuged at 100,000×g for 60 minutes. The supernatants representing the soluble enzyme are subjected to ammonium sulfate fractionation: 0–25%, 25–50%, 50–75%, >75% or 0–40% and 40–80%, b adding ammonium sulfate salt to the supernatants while stirring on ice. The solution is then stirred for 20 minutes and centrifuged in a Sorval RC-58 refrigerated centrifuge at 10,000×g for 30 minutes. After the third centrifugation, the precipitates from the ammonium sulfate fractionation steps are separately redissolved in Tris-Cl and 1 mM DTT, pH 7.4 buffer, and all fractions are dialyzed extensively against the same buffer before further steps. All purification steps were carried out at 4° C.

Synthetic Peptide Substrate

To assay for a protease or proteases that cleave in the vicinity of the N-terminus of the β-protein, an $^{125}$I-labeled peptide having the sequence His-Ser-Glu-Val-Lys-Met-Asp-Ala-Glu-Phe (peptide "P1") [SEQ. ID NO. 1] was synthesized corresponding to the β-PP sequence flanking that site. The peptide starts five amino acids upstream from the N-terminus (the aspartic acid, "D", is at the N-terminus of the β-protein) and extends across the putative cleavage site into the β-protein itself; histidine, "H", was added for purpose of radioiodination (that is, histidine replaces the isoleucine that appears at that site in the native β-protein). Labeled peptide was incubated with brain fractions of varying purity and the resulting fragments were separated by thin layer chromatography ("TLC"); N-terninal fragments were detected by autoradiography. The site of cleavage for an unknown cleavage product is then determined either by direct sequence analysis of the cleavage product, or by comparing the unknown cleavage product with cleavage products resulting from a known enzyme such as cathepsin G. Proteolytic activities from AD brain can also be examined by Western blots using full length β-PP derived from rat brain, or recombinant human β-PP produced in baculovirus, as a substrate.

Assay for Synthetic Peptide Substrate Degrading Activity

The different protease fractions are monitored for proteolytic activity against iodinated peptide "P1". Incubations are carried out at 37° C. in 50 mM Tris-Cl, pH 7.4, in the presence of 1 mM $MgCl_2$+1 mM DTT. The proteolytic products are separated by TLC on cellulose microcrystalline plates, using n-butanol:pyridine:acetic acid:water, 15:10:3:12 (v/v), as a solvent, followed by autoradiography. After TLC and autoradiography, radioactive products from the conversion of His-Ser-Glu-Val-Lys-Met-Asp-Ala-Glu-Phe [SEQ. ID NO. 1] to His-Ser-Glu-Val-Lys-Met [SEQ, ID NO. 2] were quantified with a Molecular Dynamics ImageQuant™ v3.0 scanning densitometer or a Bioscan system 200 imaging scanner. Activity of the metalloprotease was reported as the percentage of His-Ser-Glu-Val-Lys-Met-Asp-Ala-Glu-Phe (P1) [SEQ. ID NO. 1] present at time zero converted to His-Ser-Glu-Val-Lys-Met (Met cut) [SEQ. ID NO. 2] after the appropriate incubation time. The relationship is linear from 0 to approximately 60% conversion. One unit of Met cut metalloprotease activity under these conditions was defined as converting 1 μg of P1 to His-Ser-Glu-Val-Lys-Met [SEQ. ID NO. 2] in 1 min.

Purification of Metalloprotease. First Embodiment

Affigel Blue Affinity Chromatography. Affigel Blue can be used for the first chromatographic step, as it purifies the protease pool from serum albumin and a large number of other protein species. Affigel Blue (Bio-Rad) (1.5 cm×33 cm) is equilibrated to 50 mM Tris-Cl+1 mM DTT, pH 7.4, and eluted with a linear gradient of 0 to 0.5M NaCl. The flow rate is 20 ml/hour, and 3 ml fractions are collected.

First DEAE-Ion Exchange Chromatography. A pool from the Affigel Blue containing the protease activity, as detected using TLC, is loaded on a DEAE-Trisacryl M ion exchange column (1.5 cm×10 cm). The column is equilibrated with 50 mM Tris-Cl+1 mM DTT, pH 7.4, and eluted with a linear gradient of 0 to 0.5M NaCl at a flow rate of 20 ml/hour, and 3 ml fractions are collected. FIG. 5 shows the metalloprotease activity in fractions purified from brain homogenates from AD patients using DEAE-Trisacryl M ion exchange chromatography as described above. The activity that cleaves after the amino acid lysine, "K", is referred to as "Lys cut" activity and the activity that cleaves after the amino acid methionine, "M", is referred to as "Met cut" activity. The activities were separately pooled as a Met cut pool and a Lys cut pool.

Gel Filtration Chromatography. The Met cut protease activity-positive pool from the first DEAE-Trisacryl M gel filtration step is concentrated to 2.5 ml by ultrafiltration through an Amicon filter (YM-10, 10 kDa cutoff) under nitrogen. The concentrated pool is then loaded on a Sephacryl S-200 gel filtration column (2.5 cm×66 cm), equilibrated and eluted with 50 mM Tris-Cl+1 mM DTT, pH 7.4. The flow rate is adjusted to 25 ml/hour, and 2.2 ml fractions are collected.

Second DEAE-Ion Exchange Chromatography. The pool from the Sephacryl S-200 column containing the protease activity is chromatographed on a second DEAE-Trisacryl M ion exchange column (1.5 cm×4.5 cm) with a gradient of 0 to 0.5M NaCl in 50 mM Tris-Cl+1 mM DTT, pH 7.4. The flow rate is adjusted to 20 ml/h, and 2.2 ml fractions are collected.

Thiopropyl Sepharose 6B Affinity Chromatograph. In a final step, the pool from the second DEAE-Trisacryl M gel filtration step containing the protease activity is concentrated to 3 ml by ultrafiltration as before. The concentrated pool is dialyzed overnight in two changes of 500 ml 50 mM Tris-Cl, pH 7.4, to remove the DTT. The thiopropyl sepharose 6B resin (0.4 g) is washed with degassed 50 mM Tris-Cl, pH 7.4, followed by 50 mM Tris-Cl+0.3M NaCl, pH 7.4, and 2 ml of the following: 50 mM Tris-Cl+5 mM 2-mercaptoethanol, pH 7.4, and 50 mM Tris-Cl+10 mM 2-mercaptoethanol, pH 7.4. The flow rate is adjusted to 4 ml/hour, and 2.2 ml fractions are collected.

Purification of Metalloprotease, Second Embodiment

DEAE-Trisacryl M Ion Exchange Chromatography. The 40 to 80% ammonium sulfate fraction, which contained the majority of the activity, was applied on a DEAE-trisacryl M ion exchange column (1.5×20 cm). The column was previously equilibrated with 50 mM Tris-acetate+1 mM DTT, pH 7.4. Fractionation was carried out by eluting with a linear gradient of 0 to 0.5M NaCl at flow rate of 20 ml/h. Three ml fractions were collected. The elution profiles of the Met cut and Lys cut activities are shown in FIG. 8. Active Met cut fractions were pooled and dialyzed overnight against 50 mM Tris-acetate+0.5M $(NH_4)_2SO_4$+1 mM DTT, pH 7.4.

Phenyl Sepharose Hydrophobic Interactions Chromatography. The dialyzed Met cut pool was loaded on a phenyl sepharose CL-4B column (1.6×2.6 cm). Proteins were eluted with a linear gradient (300 ml total) from 0.5 to 0M $(NH_4)_2SO_4$ in the same buffer at a flow rate of 20 ml/hour, and 3.7 ml per fraction was collected. The fractions were assayed for Met cut and Lys cut activity as shown in FIG. 9. The Met cut protease eluted as a broad peak between 0.15M and 0M $(NH_4)_2SO_4$, and the fractions containing predominantly Met cut activity were pooled as indicated by the arrow in FIG. 9.

Sephacryl S-200 Gel Filtration Chromatograph. The active Met cut fractions from phenyl sepharose chromatography were pooled and dialyzed against 50 mM Tris-acetate+1 mM DTT, pH 7.4, and concentrated to 3.8 ml by ultrafiltration under nitrogen pressure in an amicon filter (YM-10, 10 kDa cut off). The concentrated pool was then loaded on a sephacryl S-200 gel filtration column (2.5×63 cm) equilibrated and eluted with 50 mM Tris-acetate+1 mM DTT, pH 7.4. The flow rate was adjusted to 10 ml/hour, and 2.5 ml fractions were collected. The Met cut protease separated from the bulk of other proteins as can be seen in FIG. 10.

HA-Ultrogel Hydroxyapatite Chromatography. In the last step the pool containing protease activity from the sephacryl S-200 column was chromatographed on a HA-ultrogel column (1.6×6.5 cm). The pool and the column were equilibrated with 10 mM $KH_2PO_4$+1 mM DTT, pH 7.4. The column was eluted with a linear gradient (100 ml total) of 10 mM to 0.3M $KH_2PO_4$+1 mM DTT, pH 7.4, at 5 ml/hour. Fractions of 1.5 ml were collected. The fractions were assayed for Met cut activity and the activity profile is shown in FIG. 11. The Met cut activity eluted at the beginning of the gradient in a sharp peak. This peak was pooled, concentrated and used as the final protease preparation.

Despite the use of various chromatographic techniques, we have been unable to separate the Met cut and Lys cut activities from each other. Thus, we concluded that the Met cut protease is also able to cleave between the Lys and the Met amino acids of the synthetic substrate but to a lesser extent (~30% of the total activity).

Chromatography of the 40 to 80% ammonium sulfate fraction on a DEAE-trisacryl M, phenyl sepharose, sephacryl S-200, and HA-ultrogel provided an approximately 114-fold purification of the Met cut protease with an overall yield of 16% (Table I, n.d. not detected).

Characterization of Metalloprotease

Molecular Weight Determination.

The molecular weight of the metalloprotease can be estimated by gel filtration using a Sephacryl S-200 (2.5 cm×66 cm) column equilibrated with 50 mM Tris-Cl+1 mM DTT, pH 7.4. The column is eluted with the same buffer at 25 ml/hour, collecting 2.2 ml fractions. The fractions are assayed for proteolytic activity as described above. Protein standards for calibration of the column include β-amylase (200,000 Da), alcohol dehydrogenase (150,000 Da), albumin (66,000 Da), carbonic anhydrase (29,000 Da), and cytochrome C (12,400 Da).

With reference now to FIG. 12, the apparent molecular weight of the metalloprotease can also be determined by SDS-PAGE. Molecular weight standards include: Myosin (H-chain) (228,000 Da), phosphorylase B (109,600 Da), bovine serum albumin (70,000 Da), ovalbumin (44,100 Da), carbonic anhydrase (27,900 Da) and β-lactoglobulin (19,000 Da). Gels were silver-stained using a Bio-Rad silver stain kit according to the manufacturer's instructions (Bio-Rad, Richmond, Calif.). The silver-staining revealed only two bands, and the bands were quantified with a Molecular Dynamics ImageQuantf™ v3.0 scanning densitometer. The lower molecular weight species accounted for about 67% of the preparation, and corresponded to an apparent molecular weight of 43 kDa. The higher molecular weight species with an apparent molecular weight of 85 kDa accounted for about 33% of the preparation. The metalloprotease was found to have a molecular weight of about 85 kDa.

Purity of the Metalloprotease

The metalloprotease was found to co-purify with another protease, prolyl endopeptidase, at all steps. Prolyl endopeptidase does not appear to cleave P1, but it can cleave β-PP. In each of our assays the prolyl endopeptidase activity was inhibited with di-isofluorophosphate, as specific inhibitor of the endopeptidase, to ensure that the assays reflected only the activity of the metalloprotease.

pH Optimum of the Purified Metalloprotease.

The metalloprotease was incubated as described above except that the buffers were a series of citrate/phosphate buffers with pH's ranging from 4.0 to 7.6. The purified metalloprotease exhibited a pH optimum around pH 6.0. The enzyme was inactive below pH 5.0 or above pH 7.6, as is shown in FIG. 13.

Mechanistic Examination of the Purified Metalloprotease

Referring now to Table II, the effects of various additives on the activity degrading the synthetic substrate (P1) were examined. The metalloprotease sample as incubated with the appropriate amount of additive and assayed for remaining activity, as described above. Control reactions with no reagent, or containing only the solvent of the reagent were always included. Reactions were allowed to proceed for 45 min at 4° C., except E-64 which was incubated for 15 or 30 min (b and c respectively) and iodoacetamide was incubated at 37° C. for 30 min.

Stock solutions of phenylmethylsulfonyl fluoride (PMSF)", E-64, 1,10 phenanthroline, calpain inhibitor, Z-Phe-Phe-$CH_2$F (Enzyme Systems Products, Livermore, Calif.) were dissolved in ethanol. Bestatin, EGTA, EDTA, HMB, iodoacetamide, leupeptin, N-ethylmaleimide, TIMP-2, CPP-Ala-Ala-Phe-pAB were dissolved in double distilled water. ZINCOV (Calbiochem, Calif.) and phosphoramidon (Sigma, USA), were also dissolved in water. Pepstatin A was dissolved in methanol. The susceptibility of the protease activity to various divalent cations was determined by including metals at a final concentration of 2 mM in the assay reaction mixture.

FIG. 6 shows the effect of DTT on AD metalloprotease activity. Samples having AD metalloprotease activity were incubated with P1 in the presence of increasing concentrations of DTT and the activity was assayed using TLC. Indicated DTT concentrations: A, DTT solvent alone (no DTT); B, 5.0 mM DTT; C, 2.5 mM DTT; D, 1.0 mM DTT; E, peptide alone (no DTT, no solvent).

FIG. 7 illustrates effects of inhibition by various agents on metalloprotease activity in fractions prepared as described above from brain homogenates from AD patients. The AD metallo-proteolytic factor preparation and the inhibitor (at the indicated concentrations) were incubated at 0° C. for 30 min and then assayed for remaining activity. Lane identifications in FIG. 7 are as follows: lane A, $H_2O$; lane B, Na iodoacetate, 5 mM; lane C, E-64 (Sigma), 0.2 mM; lane D, E-64, 0.1 mM; lane E, p-hydroxymercuribenzoate, 5 mM; lane F, N-ethylmaleimide, 5 mM; lane G, o-phenanthroline, 4 mM; lane H, o-phenanthroline, 1.8 mM; lane I, ethanol; lane J, ethanol/$H_2O$; lane K, PMSF, 5 mM; lane L, bestatin, 0.02 mM; lane M, EGTA, 5 mM; lane N, $CaCl_2$, 2 mM; lane O, DTT, 5 mM; lane P, peptide alone.

Referring now to Table II, strong inhibition of the metalloprotease was observed with N-ethylmaleimide and hydroxymercurybenzoate, less by E-64. The inhibition of the hydroxymercurybenzoate was readily reversed at stoichiometrically increasing concentrations of the reducing agent (DTT). Iodoacetamide and leupeptin had a partial inhibitory effect on the protease (34 and 36.3%, respectively). A reducing agent, i.e., dithiothreitol, was required for the activity of the metalloprotease at low concentration. Strong inhibition was obtained by 1,10-phenanthroline, ZINCOV (a chelator of Zn(II)), EDTA and EGTA suggesting the requirement for a metal. It was only after including a relatively high concentration of EGTA (7.5 mM) that we achieved inhibition of the metalloprotease with this reagent. EGTA is known to be less potent in chelating zinc and magnesium when compared to calcium. CPP-Ala-Ala-Phe-pAB, a specific inhibitor of endopeptidase 24.15, strongly inhibited the metalloprotease. To further assess the metal requirements of the protease, the enzyme activity was assayed in the presence of a number of divalent ions at 2 mM concentration. The protease was slightly activated in the presence of Mg(II) (30.4%), less by Mn(II), while Ca(II) had no significant effect on the metalloprotease activity. Strong inhibition occurred in the presence of Zn(II), Cu(II) and Hg(II).

Assay for Substrate Specificity of Purified Metalloprotease Pool

To examine the substrate specificity of the purified metalloprotease pool, aliquots of the purified active fraction were electrophoresed on SDS- substrate gels, containing 1 mg/ml casein or gelatin. The metalloprotease pool was mixed in a 1:1 ratio ("1:1") with 2× Laemmli sample buffer without mercaptoethanol and loaded on a 12% SDS polyacrylamide gel containing 2× the usual amount of ammonium persulfate. Electrophoresis was carried out at 4° C. at 20 mA. After electrophoresis, the SDS was removed by shaking the gel in 2.5% Triton X-100 for 30 min. at 25° C. The gel was then incubated in 50 mM Tris-Cl+1 mM $CaCl_2$ for 2 days at 37° C. while shaking. The gel was stained in 0.5% Coomassie brilliant Blue and destained. No activity was observed with either of the two substrates.

Alternatively, purified metalloprotease was mixed (1:1) with 0.1M Tris-acetate+10% (v/v) glycerol, pH 7.0. The samples were then subjected to native PAGE in the Davis system (Davis, 1964) using 7.5% acrylamide, containing 1 mg/ml casein or gelatin. Electrophoresis was carried out at 25 mA at 4° C. Following electrophoresis the gel was incubated in 50 mM Tris-acetate+1 mM $MgCl_2$+1 mM DTT, pH 7.4, overnight at 37° C. while shaking. The gel was stained in 0.1% Coomassie brilliant blue and destained. Z-Val-Lys-Lys-Arg-AFC (a cathepsin B substrate; SEQ ID NO: 11), and Z-Phe-Arg-AFC (a cathepsin L substrate; SEQ ID NO: 11) enzyme overlay membranes were purchased from Enzyme Systems Products, Livermore, Calif. The purified protease was mixed (1:1) with 0.1M Tris-acetate+ 10% glycerol, pH 7.0, sample buffer and subjected to native PAGE as above. Following electrophoresis the gels were incubated in 50 mM Tris-acetate+2 mM $MgCl_2$+1 mM DTT, pH 7.4, for 15 min at 25° C. then placed on a moist filter paper inside an humidity chamber. At the same time the enzyme overlay membranes were dipped quickly in the same buffer and layered on top of the gels. The gels and the attached membranes were incubated at 37° C. for 30 min. Activity was monitored with an ultraviolet (UV) lamp. There was no activity against either of these substrates.

Characterization of Substrate of Metalloprotease

The activity of purified AD metalloprotease obtained as described above was also assayed against a number of chromogenic substrates and fall length β-PP. The protease was incubated with 2 mM substrate solutions of MeO-Suc-Glu-Val-Lys-pNA, MeOSuc-Glu-Val-Lys-Met-pNA(SEQ ID NO: 12), MeOSuc-Ala-Ala-Pro-Met-pNA(SEQ ID NO: 13), Leu-pNA, Lys-pNA, Ala-pNA, and Met-pNA in 50 mM Tris-Cl, 50 mM $CaCl_2$, 100 mM NaCl, 1 mM DTT, pH 7.9., or in 50 mM Tris-acetate+2 mM $MgCl_2$+2 mM 2-mercaptoethanol, pH 7.4. Changes in absorbance were followed at 410 nm in a Titertek Multiskan™ ELISA reader. Control reactions contained no enzyme or no substrate. The purified metalloprotease was inactive towards these paranitroanilide substrates, as well as azocasein.

The activity of the metalloprotease was tested against full length β-PP purified from rats or against full length recombinant human β-PP produced in baculovirus. The reactions against rat β-PP were incubated overnight at 37° C. in 50 mM Tris-Cl, pH 7.4, 1.2 mM DTT, 1.7 mM $MgCl_2$, and the reactions against recombinant human β-PP were incubated for 15, 35 and 60 min, at 37° C. in citrate/phosphate, pH 7.0, buffer. The products were separated on discontinuous 7.5% SDS-PAGE. The separated polypeptides were transferred to PDVF membranes (Millipore) generally as described in Towbin et al. (1979), *Pro. Natl. Acad. Sci. USA*, Vol. 76, p. 4350.

The blots using the rat β-PP were immunostained with rabbit anti-β-PP antibody targeted to the area flanking the N-terminus of the β-peptide, and β-PP fragments were detected using goat anti-rabbit alkaline phosphatase and the appropriate color substrate. The blots using the recombinant human β-PP were immunostained with rabbit antibodies targeting the last 30 amino acids of the COOH—terminus of β-PP (Yamaguchi et al., 1990) and β-PP fragments were detected by using the ECL Western blotting detection system (Amersham, USA).

In order to prove specificity, the antibody was preabsorbed with its antigen (5 μg peptide/ml antibody) overnight at 4° C. The molecular weight standards used were: ovalbumin (44,000 Da), carbonic anhydrase (27,900 Da), b-lactoglobulin (19,000 Da), lysozyme (14,300 Da), bovine trypsin inhibitor (6,200 Da), insulin (a and β chains, 3000 Da). The C-100 is a recombinant polypeptide which corresponds to the 596–695 amino acids of β-PP 695.

Several proteolytic products were revealed including a prominent band comigrating with the C-100 polypeptide which represents the 596–695 amino acids of β-PP 695, as shown in FIG. 14, panel A. Judging from its molecular weight, this proteolytic fragment contains the β-protein segment. The staining of the fragment was completely abolished when the antibody was preincubated with its antigen, as shown in FIG. 14, panel B.

Digestion, HPLC and Peptide Sequence Analysis

Protein sequence analysis was performed according to the method of Aebersold et al, 1987, with the following modifications. The proteins were separated on a 10% SDS-PAGE gel and electroblotted in a Bio-Rad system onto nitrocellulose for 2 h. The NaOH wash was omitted to minimize loss of protein, and the digestion buffer was modified as in Fernandez et al. (1992). After digestion with lys C endopeptidase, the solution was stored at −20° C. until separation of the resultant peptides by narrowbore reverse-phase HPLC which was performed on a Hewlett-Packard 1090 PLC equipped with a 1040 diode array detector, using a Vydac 2.1 mm×150mm C18 column. The gradient employed was 5% B at 0 min, 33% B at 63 min, 60% B at 95 min and 80% B at 105 min at a flow rate of 150 μl/min, where buffer A was 0.06% trifluoroacetic acid/water and buffer B was 0.055% trifluoroacetic acid/acetonitrile. Chromatographic data at 210, 277 nm, and UV spectra from 209 to 321 nm of each peak were obtained. While monitoring absorbance at 210 nm, fractions were manually collected by peak into 1.5 ml microfuge tubes and immediately stored without drying at −20° C. in preparation for peptide sequence analysis. Optimal fractions for Edman microsequencing were screened for length and homogeneity by mass analysis on a Finnigan Lasermat time-of-flight mass spectrometer. 1 or 2 ml of each fraction was mixed with 0.5 ml of a-cyano-4-hydroxycinnamic acid matrix and applied to the sample target. Spectra were acquired by summing the results of 5 to 10 laser pulses at the lowest power which gave a signal to noise ratio of greater than 4:1. Details of strategies for the selection of peptide fractions and their microsequencing have been previously described (Lane et al, 1991). Samples for amino terminal sequence analysis were applied directly to a polybrene pre-cycled glass fiber filter and placed in the reaction cartridge of an ABI Model 477A protein sequencer. The samples were subjected to automated Edman degradation using the manufacturer's recommendations for faster cycle time (30 min) by decreasing dry-downtimes and increasing reaction cartridge temperature to 53° C. during coupling. The resultant phenylthiohydantoin amino acid fractions were manually identified using an on-line ABI Model 120A HPLC and Shimadzu CR4A integrator.

Internal fragments of both the 85 kDa and the 43 kDa bands were obtained A after digestion. Two peptides from the 85 kla protein were sequenced and revealed a high degree of homology with sequences from rat metalloendopeptidase 24.15 [SEQ. ID Nos. 3 and 5]. The sequences are compared in Table III, human sequence-peptide, 85-1 is SEQ ID No. 4 and human sequence-peptide 85-2 is SEQ ID No.6. We were unable to obtain sequence from a third fragment because its $NH_2$-terminus was blocked suggesting that it is the $NH_2$-terminus of the protease. Similarly, sequences obtained from two fragments of the 43 kDa band revealed identity to sequences of rat aspartate aminotransferase (EC 2.6.1.1) [SEQ. ID Nos. 7 and 9], an ubiquitous pyridoxal phosphate-dependent enzyme (Braunstein and Snell, 1985). These sequences are compared in Table IV, human sequence peptide 43-1 is SEQ ID No. 8and human sequence peptide 43-2 is SEQ ID No. 10. Human aspartate aminotransferase was purchased from Sigma and assayed with the synthetic substrate P1. No proteolytic activity was observed under our incubation conditions.

Isolation and Characterization of Serine AD Proteolytic Factor

The following is a detailed description of identification and purification of an AD proteolytic factor that includes a $Ca^{2+}$ activated serine protease whose P1 cleaving activity is inhibited by ACT and PN2.

Brain fractions were incubated with the iodinated peptide ($^{125}$I-P1) and treated with disuccinimidyl suberate ("DSS") to crosslink any proteins that were in intimate contact with the peptide, i.e., to crosslink any enzyme-substrate complex (and, in this instance, any protease-substrate complexes. Enzyme-substrate complexes, stabilized by the DSS crosslinking were detected on SDS gels. N-terminal fragments of 125I-P1 were detected following incubation with various fractions by autoradiography of TLC plates, generally as described above in the detailed protocol for the AD metalloprotease.

Employing these assays (TLC, DSS crosslinking), a specific serine protease activity was partially purified from Alzheimer's brain homogenates by classical liquid chromatography.

Figure 1:
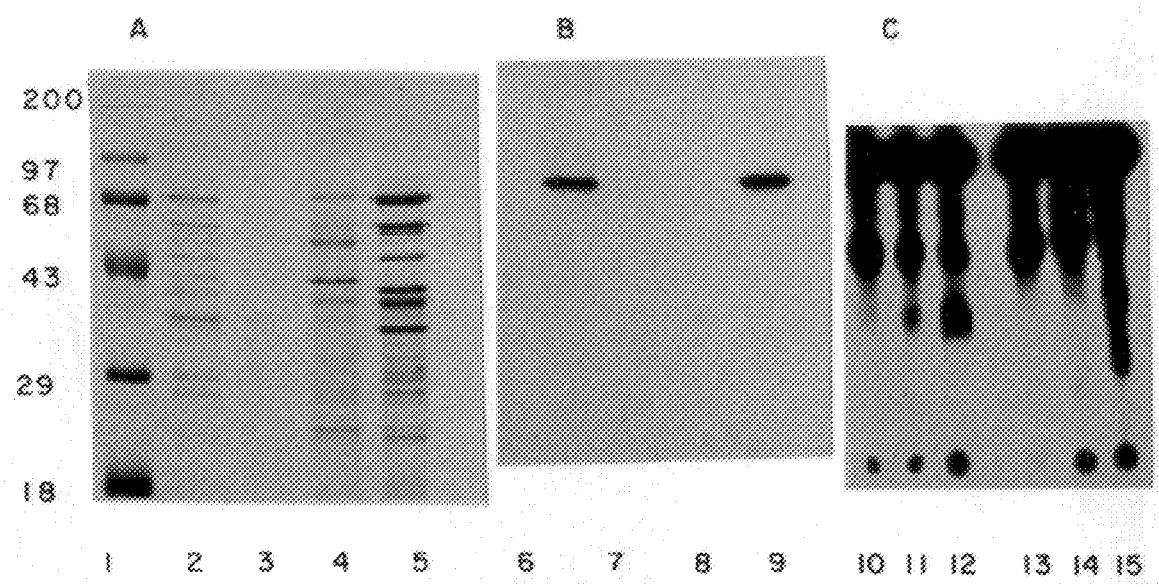

Results of an initial purification of specific protease activity from Alzheimer's disease brain ("AD brain") are shown in FIG. 1. Brain homogenates were prepared in phosphate buffered saline ("PBS") (20 mM phosphate buffer pH 7.0, 0.15 M NaCl) and 1 mM dithiothreitol ("DTT"), and spun at 10,000 g. The supernatant was dialyzed against PBS(A) (20 mM phosphate buffer pH 7.0, 20 mM NaCl) and 1 mM DTT, and applied to DE52-cellulose (Whatman) equilibrated with 10 mM Tris-HCl (pH 7.0, 20 mM NaCl) and 1 mM DTT; the column was extensively washed and bound proteins were eluted with 0.5 M NaCl. The active fraction was further purified by ammonium sulfate precipitation, followed by dialysis.

The purification was monitored by a peptide degradation assay as follows. All fractions were incubated with iodinated peptide 1 ("$^{125}$I-P1", amino acid sequence His-Ser-Glu-Val-Lys-Met-Asp-Ala-Glu-Phe [SEQ. ID NO. 1]) in 10 mM Tris-HCl (pH 7.6, 1 mM CaCl) for one hour, and then the cleavage products were separated by TLC on cellulose microcrystalline plates (J. T. Baker), followed by autoradiography (FIG. 1, panel C). The TLC solvent was n-butanol:pyridine:acetic acid:water (15:10:3:12 by volume) as described generally in P. Tempst et al. (1983), *Eur. Jour. Biochem.*, Vol. 135, pp. 321–330. Fractions were also reacted with $^{125}$I-P1 for 30 minutes at 4° C., crosslinked with 0.5 mM DSS for 15 minutes at room temperature, and subjected to SDS-PAGE, and the gel was stained with coomassie blue (FIG. 1, panel A), dried and exposed to X-ray film (FIG. 1, panel B).

Lane identifications in FIG. 1 are as follows: lane 1, Mw standards; lanes 2, 6, 15, DE52 column flowthrough fraction; lanes 3, 7, 10, ammonium sulfate ("AS") precipitation, 0–25% saturation; lanes 4, 8, 11, 25–50% AS; lanes 5, 9, 12, 50–75% AS; lane 13, .75% AS; lane 14, untreated $^{125}$I-P1. The asterisk (*) indicates the minor 30 kDa band. Further purification, including a 100,000 g spin in PBS followed by solubilization of the pellet in 1% Triton X-100 in PBS and a second spin at 100,000 g, revealed that following these treatments the enzymatic activity is found in both the soluble fraction and the membrane-bound fraction.

Figure 2A:
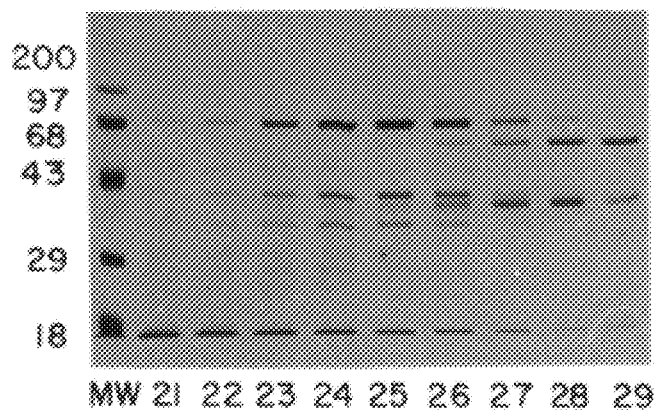
FIG. 2 is a series of prints showing serine protease activity in fractions from brain homogenates from AD patients, further purified by size exclusion chromatography. The respective panels A, B, C are as described in FIG. 1.
Figure 2B:
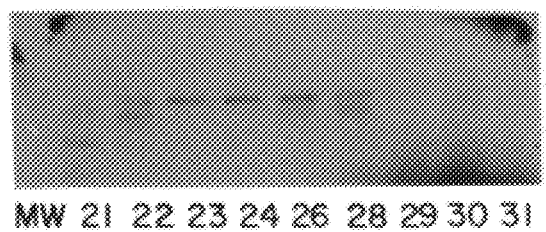
Figure 2C:
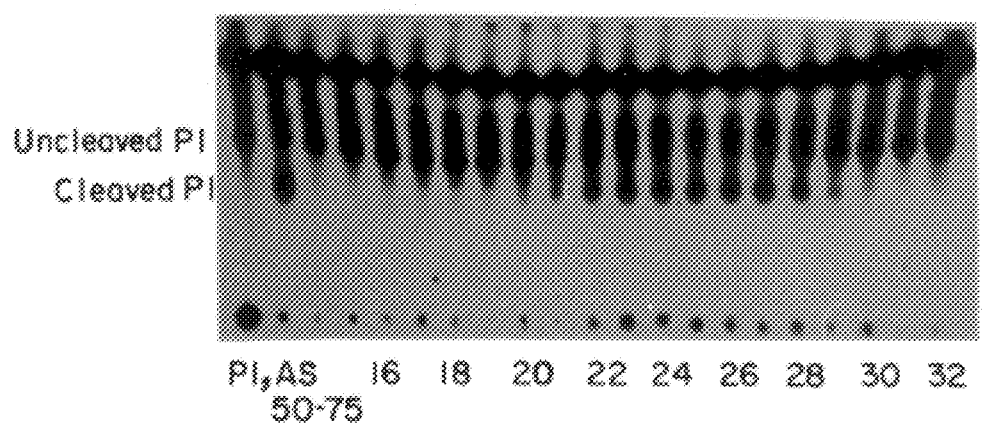

Results of purification of a specific serine protease from AD brain by size exclusion chromatography are shown in FIG. 2. An ammonium sulfate fraction 50–75%, obtained as described above, was dialyzed, applied to a mono Q column (Pharmacia) and eluted with a 20–500 mM NaCl gradient in 10 mM Tris HCl, pH 7.0, with 1 mM DTT. Fractions demonstrating activity were concentrated and applied to a Sephadex S-300 column (Pharmacia) and eluted with 10 mM Tris-HCl, pH 7.0, 200 mM NaCl, and 1 mM DTT.

Panels A, B and C in FIG. 2 are as in FIG. 1. Analysis of S-300 column fractions 14 to 32 is shown; fraction numbers are indicated. The first lane in Panel C is untreated $^{125}$I-P1; the second lane is fraction AS 50–75% (before S-300 separation). Fractions 23–28 were reserved for further analysis.

A single protein was radioaffinity labeled (FIG. 1) following initial purification. Subsequent steps of purification resulted in a major protein of approximately 68 kDa (FIGS. 1 and 2) and a minor one at 30 kDa (FIG. 1).

Figure 3:
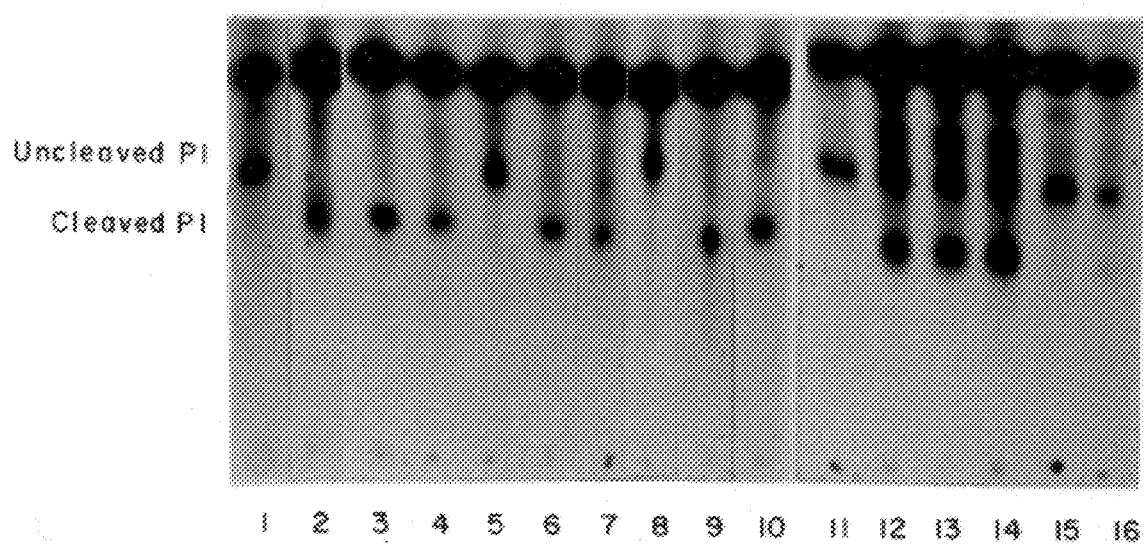
FIG. 3 is a print showing inhibition by various agents of serine protease activity in fractions from brain homogenates from AD patients.

FIG. 3 illustrates effects of inhibitors on the protease activity of the serine AD proteolytic factor isolated as described above. A peptide degradation assay, using 0.1 μg $^{125}$I-P1 for each trial as described above with reference to FIG. 1, was used. Lane identifications in FIG. 3 are as follows: lanes 1 and 11, no protease; lanes 10 and 12, the protease fraction alone ("PF"); lanes 2–9 and 13–16, the protease fraction was treated for 15 minutes at room temperature with various agents, then the P1 was added and the mixture incubated at 37° C. for 1 hour (except lane 9, which was incubated for 20 hours); lane 2, PF with PN1, 1 μM; lane 3, PF with ACT, 0.4 μM; lane 4, PF with ACT, 1 μM; lane 5, PF with ACT, 1.5 μM; lane 6, PF with PN2, 0.2 μM; lane 7, PF with PN2, 0.4 μM; lane 8, PF with PN2, 0.75 μM, for 1 hour; lane 9, PF with PN2, 0.75 μM, for 20 hours; lane 13, PF with β-mercaptoethanol, 0.5 mM; lane 14, PF with 2 mM $Ca^{2+}$; lane 15, PF with 2 mM EGTA; lane 16, PF with 1 mM DFP.

EGTA, an inhibitor of $Ca^{2+}$ dependent proteases, and DFP, an inhibitor of serine proteases, prevent cleavage of the $^{125}$I-P1 by the AD proteolytic factor (FIG. 3), indicating that the fraction was enriched in a $Ca^{2+}$ activated, serine protease. Additional $Ca^{2+}$ enhances the degradation (FIG. 3, lane 14). In addition, two serine protease inhibitory proteins from human brain that may be involved in regulating the degradation of β-PP, ACT (Calbiochem) and purified PN2 (secreted β-PP), also inhibited cleavage of P1 by the AD proteolytic factor. The complex of the AD proteolytic factor protease with PN2 is reversible; compare lane 8 (1 hr incubation) with lane 9 (20 hrs incubation). In contrast, protease nexin 1 and albumin did not influence the activity of the AD proteolytic factor.

The Kunitz-type protease inhibitors are identical to the inhibitor protease nexin 2 ("PN2", described, for example, in W. E. Van Nostrand et al. (1989), *Nature*, Vol. 341, pp. 546–49; T. Oltersdorf et al. (1989), *Nature*, Vol. 341, pp. 144–47.

Sequences of the peptide 1 cleavage products generated by cathepsin G and some other common proteases were compared to those generated by the serine AD protease fraction; the results of a comparison of P1 cleavage products for $Ca^{2+}$ activated specific serine protease ("CASP") from Alzheimer's disease brain and cathepsin G on peptide 1 are shown in FIG. 4. Five micrograms of unlabeled peptide was incubated with the enzymes in 10 mM Tris-HCl, pH 7.6, 1 mM $CaCl_2$ for 15 hours at 37° C. Resulting mixtures were analyzed by direct peptide sequencing as described generally in P. Tempst et al. (1989), *Anal. Biochem.*, Vol. 183, pp. 290–300; the percentage cleavage of each peptide bond is indicated under the arrows. Unseparated proteolytic fragments were directly sequenced as a mixture. Of the enzymes tested, only cathepsin G and the AD proteolytic fraction cleaved P1 before and after the methionine, and thus only they among these enzymes are capable of generating the cleavage to release the N-terminus of the β-protein from the β-protein precursor. Although cleavage kinetics of the AD proteolytic factor are relatively slow, a presence of active AD proteolytic factor in brain would ensure accumulation of the β-protein over time. The partially purified AD protease cleaves the Asp-Ala bond (FIG. 4) which would result in a β-protein missing the N-terminal Methionine. Cathepsin G is not detectable in human brain tissue using immunohistochemistry or Western or northern blot analysis.

The calcium-activated AD proteolytic factor cleaves metabolically labelled endogenous β-PP substrate as well as the P1 peptide. Labelled $^{35}$S-β-PP, made as described in S. Sisodia et al. (1990), *Science*, Vol. 248, pp. 492–95 and obtained from S. Sisodia, was incubated with the AD proteolytic factor, and the fragments were separated on gel and the gel was autoradiographed. A mixture of proteases appear to be present, and one or more than one of these may play a role in an alternative pathway in the brains of persons having abnormal amyloid deposits.

In addition to being able to degrade the synthetic P1, the serine protease fraction also degraded purified human PN2, and metabolically labeled $^{35}$Met-PN2 secreted into the medium by cells transfected with the human β-PP770. Other labeled secreted proteins were not affected by the protease.

Thus far, two protease inhibitors have been described that may be involved in amyloid deposits of the β-protein type: β-PP (PN2) (the β-protein precursor) and ACT. In the brain, the two forms of the β-PP, one having the protease inhibitory domain (751/770 amino acids) and the other lacking it (695 amino acids), are found in comparable amounts, in contrast to the β-PP in other organs where the inhibitor form prevails. The different ratios of the two forms may explain the almost unique accumulation of the β-protein type amyloid in the brain, although β-protein antibodies can also label skin, intestine and adrenal sections. When the amounts of the β-PP are compared between AD and controls they do not seem significantly different, but high levels of abnormal degradative forms of β-PP are found in AD neurons and neurites and on Western blots using β-PP antibodies.

Use

In AD, and most likely in normal aging, the β-protein is probably formed as a result of an abnormal proteolytic degradation of a normal protein. The finding that the AD serine protease and, to a lesser extent, the metalloprotease cleave after lysine suggests that it may also be able to cleave at amino acids 15–17 (QKL; Q, glutamine; L, lysine) of the β-protein, the normal physiologic site of β-PP processing for secretion. Minor changes in the β-PP, an imbalance in proteases and inhibitors may influence many normal brain processes, for instance neurite extension.

An aberrant proteolytic degradation of the β-PP can contribute to amyloid deposition, which in turn may be trophic or toxic to neurons and astrocytes, causing the neuritic response, neuronal cell death and cognitive deficits. AD may be treated according to the invention by administering to the patient an inhibitor of the AD proteolytic activity according to the invention. Such an inhibitor can be, for example, a competitive inhibitor, such as a fragment of the β-PP molecule corresponding to the binding site of the proteolytic enzyme.

Likely candidates for effective inhibitors of AD proteolytic activity can be screened by incubating an AD protease according to the invention with a known specific substrate (such as a synthetic oligopeptide having an amino acid sequence corresponding to a sequence spanning the β-protein N-terminus) in the presence of a candidate agent under conditions in which the AD protease would be expected, in the absence of an inhibitor, to cleave the synthetic oligopeptide near the N-terminus. Candidate agents that effectively inhibit proteolysis in such a trial can then be tested for inhibitory effect in an in vitro model and/or in an animal model.

A preferred inhibitor is capable of crossing the blood-brain barrier, so that it can be administered parenterally or orally. Also, a preferred inhibitor is a molecule other than a peptide, so that the inhibitor will not be rapidly degraded following administration. Also, the preferred inhibitor specifically inhibits the β-PP cleaving activity of the AD protease, and does not generally inhibit the activity of brain proteases that are essential to normal metabolism.

Proteolytic fragments resulting from the action on β-PP of an AD protease according to the invention can be detected using, e.g., a battery of antibodies directed against the C-terminus and the N-terminus of the β-PP on Western blots. Such analysis can aid in establishing where the β-PP molecule is cleaved and how the β-protein may be generated. Once the production of the β-protein is carried out in vitro, inhibitors (or agents that are candidates for inhibitors) may be screened for capacity to arrest the activity of the AD protease in vitro, and in vivo in cell culture.

Monoclonal antibodies ("mAb") raised against a purified AD protease according to the invention, prepared using standard protocols, can be used to establish (and to quantify) the cellular location of the enzyme in the brain and in other tissues such as skin, kidneys, and liver. Such mAb can also be used in the screening of expression libraries, for locating and identifying AD protease-encoding genes, and for cloning such AD protease genes for use in AD protease-producing expression systems.

The damage to tissues resulting from amyloid deposition in AD appears to be irreversible. The neurological symptoms characteristic of AD appear to result from such tissue damage. For a therapy for AD according to the invention to be effective, it should be employed before amyloid deposition has substantially progressed and before neurological symptoms are manifested.

Determining the presence of, or monitoring the quantity of, AD proteases can provide a tool for early diagnosis of incipient AD. Tissue or body fluid samples such as, for example, samples of blood, CSF, saliva, urine, can be drawn and assayed for the presence of AD proteases, as an indication of a likelihood of abnormal β-PP metabolism, producing β-protein and, ultimately, causing amyloid deposition in tissues.

Other embodiments are within the following claims. For example, any crosslinking agent other than DSS can be used in the enzyme purification protocol, provided that the agent is capable of forming crosslinks in an enzyme-substrate complex between portions of the enzyme and the substrate where the enzyme and substrate are in near proximity.

TABLE II

| Reagent | Reagent conc. (mM) | % Activity Remaining |
| --- | --- | --- |
| Control | | 100 |
| N-ethylmaleimide | 5.0 | 7.9 |
| Hydroxymercury-benzoate | 1.6 | 0 |
| E-64 | 0.14 | 57.5[b] |
| " | " | 27.3[c] |
| Iodoacetamide | 8.0 | 66 |
| Calpain Inhibitor | 1.0 | 92.9 |
| Z-Phe-Phe-CH2F | 0.2 | 82.7 |
| Leupeptin | 0.2 | 63.7 |
| PMSF | 7.0 | 100 |
| Aprotinin | 0.03 | 100 |
| Soybean Trypsin Inhibitor | 0.01 | 100 |
| 1,10 phenanthroline | 4.0 | 0 |
| ZINCOV | 1.0 | 42.4 |
| Phosphoramidon | 1.0 | 89.5 |
| CPP-Ala-Ala-Phe-pAB | 0.15 | 28.0 |
| " | 0.015 | 47.5 |
| EDTA | 3.0 | 33.2 |
| EGTA | 7.5 | 0 |
| TIMP-2 | 0.03 | 100 |
| Bestatin | 0.002 | 60 |
| Pepstatin A | 0.15 | 100 |
| Dithiothreitol | 0.0 | 0 |
| " | 1.0 | 100 |
| " | 2.5 | 70.8 |
| " | 5.0 | 25.5 |
| Mg(II) | 2.0 | 130.4 |
| Mn(II) | 2.0 | 119.1 |
| Ca(II) | 2.0 | 104.0 |
| Cu(II) | 2.0 | 0 |
| Zn(II) | 2.0 | 0 |
| Hg(II) | 2.0 | 0 |

TABLE I

| Step | Volume ml | Total protein $A_{280}$ units | Total protease activity Units | Spec. Activity Units/$A_{280}$ | Purification factor | Yield % |
| --- | --- | --- | --- | --- | --- | --- |
| Crude extract | 250 | 3600 | n.d. | n.d. | — | — |
| (NH$_4$)$_2$SO$_4$ fraction (40–80%) | 50 | 59 | n.d. | n.d. | — | — |
| DEAE-Trisacryl M | 60 | 70.7 | 624 | 8.8 | 1 | 100 |
| Phenyl Sepharose | 5.8 | 8.7 | 47.6 | 5.5 | 0.6 | 7.6 |
| Sephacryl S-200 | 11 | 2.8 | 56.9 | 20.3 | 2.4 | 9.1 |
| HA-Ultrogel | 1 | 0.01 | 100.0 | 1000.0 | 113.6 | 16.0 |

TABLE III

| SOURCE | SEQUENCE | SEQ ID NO |
|---|---|---|
| Rat[a] | Ala-Leu-Ala-Asp-Val-Glu-Val-Thr-Tyr-Thr-Val-Gln[78] | 3 |
| Human Peptide 85-1 | Ala-Leu-Ala-Asp-Val-Glu-Val-Thr-Tyr-Thr-Val-Gln | 4 |
| Rat[a] | Asn-Leu-Asn-Glu-Asp-Thr-Thr-Phe-Leu-Pro-Phe-Thr-Arg-Glu-Glu-Leu-Pro[100] | 5 |
| Human Peptide 85-2 | Asn-Leu-Asn-Glu-Asp-Thr-Thr-Phe-Leu-Pro-Phe-Thr-Arg-Glu-Glu-Leu-Pro | 6 |

[a]Pierotti et al., 1990

TABLE IV

| SOURCE | SEQUENCE | SEQ ID NO |
|---|---|---|
| Rat[b] | Asn-Thr-Pro-Val-Tyr-Val-Ser-Ser-Pro-Thr-Thr-Glu-Asn-His[140] | 7 |
| Human Peptide 43-1 | Asn-Thr-Pro-Val-Tyr-Val(Ser)Xaa-Pro(Thr)Xaa-Glu-Xaa-His | 8 |
| Rat[b] | Asn-Phe-Gly-Leu-Tyr-Asn-Glu-Arg-Val-Gly-Asn-Leu-Thr-Val-Val-Gly-Lys[276] | 9 |
| Human Peptide 43-2 | Asn-Phe-Gly-Leu-Tyr-Asn-Glu-Arg-Val-Gly-Asn-Leu-Thr-Val-Val-Xaa-Xaa | 10 |

[b]Pave-Preux et al., 1988

---

What is claimed:

1. A purified endoprotease identical to an endoprotease found in brains of humans with Alzheimer's Disease, which purified endoprotease, when incubated with a peptide having an amino acid sequence of His-Ser-Glu-Val-Lys-Met-Asp-Ala-Glu-Phe (SEQ ID NO: 1), cleaves the peptide between its Met and Asp residues, which purified endoprotease is inhibited by O-phenanthroline and by metal chelators bat not by pheymethylsulfonyl fluoride.

2. An endoprotease prepared by a method comprising:
   providing a human brain tissue homogenate;
   purifying the endoprotease from the homogenate by:
   separating the homogenate into at least two fractions;
   assaying the homogenate fractions for an ability to cleave a peptide having an amino acid sequence of His-Ser-Glu-Val-Lys-Met-Asp-Ala-Glu-Phe (SEQ ID NO: 1) between its Met and Asp residues; and
   selecting those homogenate fractions whose ability to cleave the peptide between its Met and Asp residues is highest.

3. The endoprotease of claim 2 wherein the steps of separating, assaying and selecting are iterated.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:1:

His  Ser  Glu  Val  Lys  Met  Asp  Ala  Glu  Phe
    1                      5                                        1 0

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

His  Ser  Glu  Val  Lys  Met
    1                      5

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:3:

Ala Leu Ala Asp Val Glu Val Thr Tyr Thr Val Gln
1               5                   10

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

Ala Leu Ala Asp Val Glu Val Thr Tyr Thr Val Gln
1               5                   10

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:5:

Asn Leu Asn Glu Asp Thr Thr Phe Leu Pro Leu Thr Arg Glu Glu Leu
1               5                   10                  15

Gly Gly Leu Pro
            20

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i i ) IMMEDIATE SOURCE:
        ( B ) CLONE: human sequence peptide 85- 2

( x i ) SEQUENCE DESCRIPTION: SEQ ID NO:6:

Asn Leu Asn Glu Asp Thr Thr Phe Leu Pro Phe Thr Leu Gln Glu Leu
1               5                   10                  15

Gly Xaa Leu Pro
            20

( 2 ) INFORMATION FOR SEQ ID NO:7:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:7:

Asn Thr Pro Val Tyr Val Ser Ser Pro Thr Thr Glu Asn His
1               5                   10

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i i ) IMMEDIATE SOURCE:
        ( B ) CLONE: human sequence peptide 43- 1

( x i ) SEQUENCE DESCRIPTION: SEQ ID NO:8:

```
Asn  Thr  Pro  Val  Thr  Val  Xaa  Pro  Xaa  Glu  Xaa  His
1                   5                        1 0
```

( 2 ) INFORMATION FOR SEQ ID NO:9:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:9:

```
Asn  Phe  Gly  Leu  Tyr  Asn  Glu  Arg  Val  Gly  Asn  Leu  Thr  Val  Val  Gly
1                   5                        1 0                         1 5
Lys
```

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i i ) IMMEDIATE SOURCE:
        ( B ) CLONE: humzn sequence peptide 43- 2

( x i ) SEQUENCE DESCRIPTION: SEQ ID NO:10:

```
Asn  Phe  Gly  Leu  Tyr  Asn  Glu  Arg  Val  Gly  Asn  Leu  Thr  Val  Val  Xaa
1                   5                        1 0                         1 5
Xaa
```

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( i i ) MOLECULE TYPE: peptide ( v i i ) IMMEDIATE SOURCE:
        ( B ) CLONE: cathepsin B substrate ( x i ) SEQUENCE DESCRIPTION: SEQ ID NO:11:

```
Val  Lys  Lys  Arg
1
```

( 2 ) INFORMATION FOR SEQ ID NO:12:

(i) SEQUENCE CHARACTERISTICS:
    (A) LENGTH: 4 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO:12:

Glu Val Lys Met
1

(2) INFORMATION FOR SEQ ID NO:13:

(i) SEQUENCE CHARACTERISTICS:
    (A) LENGTH: 4 amino acids
    (B) TYPE: amino acid
    (C) STRANDEDNESS: Not Relevant
    (D) TOPOLOGY: Not Relevant (ii) MOLECULE TYPE: peptide (xi) SEQUENCE DESCRIPTION: SEQ ID NO:13:

Ala Ala Pro Met
1